US007608389B2

(12) United States Patent
Argitis et al.

(10) Patent No.: US 7,608,389 B2

(45) Date of Patent: Oct. 27, 2009

(54) PHOTORESISTS PROCESSABLE UNDER BIOCOMPATIBLE CONDITIONS FOR MULTI-BIOMOLECULE PATTERNING

(75) Inventors: Panagiotis Argitis, Institute of Microelectronics, NCSR "Demokritos" Aghia Paraskevi, Athens (GR) Gr-15310; Konstantinos Misiakos, Institute of Microelectronics, NCSR "Demokritos" Aghia Paraskevi, Athens (GR) GR-15310; Sotirios E. Kakabakos, Institute of Radioisotopes and Radiodiagnostic Products, NCSR "Demonkritos" Aghia Paraskevi, Athens (GR) GR-15310; Constantinos D. Diakoumakos, Athens (GR)

(73) Assignees: National Centre for Scientific Research Demokritos (GR); Panagiotis Argitis (GR); Konstantinos Misiakos (GR); Sotirios E. Kakabakos (GR)

( * ) Notice: Subject to any disclaimer, the term of this patent is extended or adjusted under 35 U.S.C. 154(b) by 0 days.

(21) Appl. No.: 10/479,293

(22) PCT Filed: May 30, 2002

(86) PCT No.: PCT/GR02/00033

§ 371 (c)(1), (2), (4) Date: Oct. 12, 2004

(87) PCT Pub. No.: WO02/097533

PCT Pub. Date: Dec. 5, 2002

(65) Prior Publication Data

US 2005/0037276 A1 Feb. 17, 2005

(30) Foreign Application Priority Data

May 31, 2001 (GR) ............................ 20010100271

(51) Int. Cl.

| | |
|---|---|
| *G03F 7/30* | (2006.01) |
| *G03F 7/32* | (2006.01) |
| *G03F 7/40* | (2006.01) |
| *G03F 7/20* | (2006.01) |
| *G03F 7/039* | (2006.01) |

(52) U.S. Cl. .................... 430/315; 430/270.1; 430/311; 430/312; 430/320; 430/321; 430/325; 430/326; 430/329; 430/331; 430/905; 430/910

(58) Field of Classification Search ....................... None
See application file for complete search history.

(56) References Cited

U.S. PATENT DOCUMENTS 4,103,064 A 7/1978 McAlear et al.

(Continued)

FOREIGN PATENT DOCUMENTS

DE 19546140 A1 6/1997

(Continued)

OTHER PUBLICATIONS

Derwent English abstract for JP2-309358.*

(Continued)

*Primary Examiner*—Sin J. Lee
(74) *Attorney, Agent, or Firm*—Porzio, Bromberg and Newman, P.C.

(57) ABSTRACT

Novel photoresist materials, which can be photolithographically processed in biocompatible conditions are presented in this invention. Suitable lithographic scheme for the use of these and analogous resists for biomolecule layer patterning on solid substrates are also described. The processes described enable micropatterning of more than two different proteins on solid substrates without denaturation of the proteins. The preferred resist materials are based on (meth)acrylate copolymers that contain at least one acid cleavable ester group and at least one hydrophilic group such as an alcoholic or a carboxylic group.

8 Claims, 7 Drawing Sheets

U.S. PATENT DOCUMENTS

Figure 1:
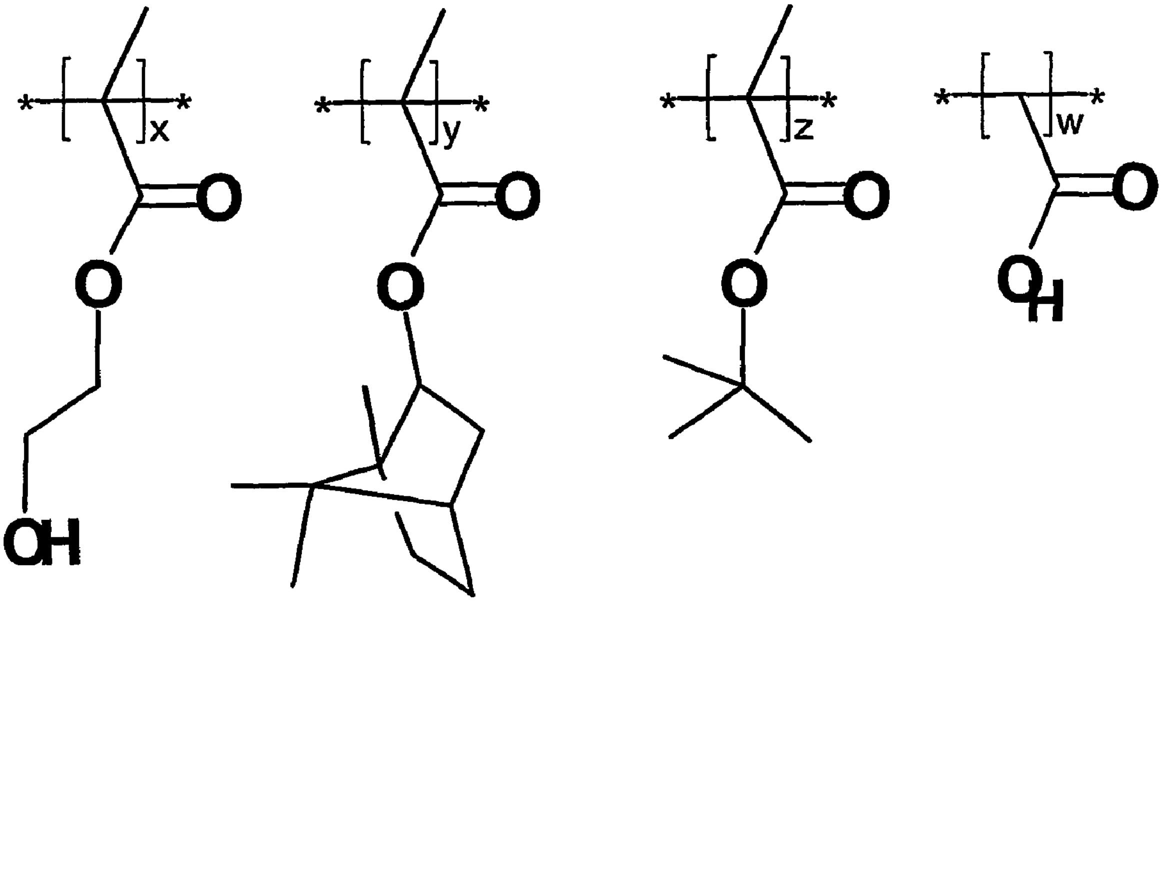

| | | | | |
|---|---|---|---|---|
| 4,103,073 | A | 7/1978 | McAlear et al. | |
| 5,688,642 | A * | 11/1997 | Chrisey et al. | 435/6 |
| 5,736,257 | A | 4/1998 | Conrad et al. | |
| 5,773,308 | A | 6/1998 | Conrad et al. | |
| 5,847,019 | A | 12/1998 | Conrad et al. | |
| 5,876,899 | A * | 3/1999 | Szmanda et al. | 430/270.1 |
| 6,063,543 | A * | 5/2000 | Hien et al. | 430/270.1 |
| 6,265,116 | B1 * | 7/2001 | Uchikawa et al. | 430/7 |
| 6,440,645 | B1 * | 8/2002 | Yon-Hin et al. | 430/322 |
| 6,723,485 | B1 * | 4/2004 | Tsutsumi et al. | 430/270.1 |
| 6,852,466 | B2 * | 2/2005 | Trefonas et al. | 430/270.1 |
| 6,884,562 | B1 * | 4/2005 | Schadt et al. | 430/270.1 |

FOREIGN PATENT DOCUMENTS

| | | |
|---|---|---|
| JP | 2-309358 | * 12/1990 |
| JP | 08183962 A1 | 7/1996 |
| JP | 10219182 A1 | 8/1998 |
| JP | 10235788 A1 | 9/1998 |

OTHER PUBLICATIONS

Database EPODOC 'Online! European Patent Office, The Hague, NL; XP002190268, cited in the application, abstract & GR 1 003 421 B (Argeitis Panagiotis; Kakampakos Sotirios; Misiakos Konstantinos; Dimokr) Sep. 1, 2000.

Douvas, A et al.: “Biocompatible photolithographic process for the patterning of biomolecules,” Biosensors & Bioelectronics., vol. 17, 2002, pp. 269-278, XP008000715, Elsevier Science Publishers, Barking, GB, ISSN: 0956-5663.

Diakoumakos, Constantinos et al.: “Dilute ageous base developable resists for environmentally friendly nd biocompatible processes” Micro and Nano Engineering 2001; Grenoble, France, France Sep. 16-19, 2001, vol. 61-62, Sep. 16, 2001, pp. 819-827.

Douvas, Antonios et al.: “Photolithographic patterning of protein with photoresists processable under biocompatible conditions” J Vac Sci Technol B Microelectron Namometer Struct; Journal of Vacuum Science and Technology B: Microelectronics and Namometer Structures Nov./Dec. 2001, vol. 19, No. 6, Nov. 2001, pp. 2820-2824.

M. M. Thompson et al., “Biosensors and the transduction of molecular recognition,” Anal. Chem., 63, 393 A, 1991.

E.P. Diamandis, T.K. Christopoulos eds, “Immunoassay,” San Diego, Academic Press, 1996.

Y. Hanazato et al., “Glucose sensor based on a field-effect transistor with a photolithographically patterned glucose oxidase membrane,” Anal. Chim. Acta, 193, 87-98, 1987.

T. Vopel et al.: “Amperometric glucose sensor with a photolithograhically patternec enzyme membrane,” Anal. Chim. Acta, 251, 117-120, 1991.

S. Britland et al.: “Micropatterning Proteins and Synthetic Peptides on Solid Supports: A Novel Application for Microelectronics Fabrication Technology,” Biotechnol. Prog., 8, 155-160, 1992.

D. Kleinfield et al.: “Controlled outgrowth of disassociated neurons on patterned substrates,” J. Neurosci. 8, 4098-4120, 1998.

H. Gao et al.: “Immunosensing with photoimmobilized immunoreagents on planar potical wave guides,” Biosens. and Bioelectronics, 10, 317, 1995.

D.V. Nicolau et al.: “Positive and negative tone patterning using conventionsl Deep-UV/e-beam Resists,” Langmuir, 15 3845, 1999.

E.D. Fabrizio et al.: “Nanometer biodevice fabrication by electron beam lithography,” J. Vac. Sci. Technol. B, 15(6), Nov./Dec. 1997.

C.S. Dulcey et al.: “Deep UV Photochemistry of Chemisorbed Monolayers: Patterned Coplanar Molecular Assemblies,” Science, 551, Apr. 1991.

D.A. Stenger et al.: “Coplanar Molecular Assemblies of Amino- and Perfluorinated Alkylsilanes: Characterization and Geometric Definition of Mammalian Cell Adhesion and Growth,” J. Am. Chem. Soc. 114, 8435, 1992.

S.K. Bhatia et al.: “New Approach to Producing Patterned Biomolecular Assemblies,” J. Am. Chem. Soc., 114, 4432, 1992.

S. K. Bhatia et al.: “Fabrication of Surfaces Resistant to Protein Adsorption and Application to Two-Dimensional Protein Patterning,” Anal. Biochemistry, 208, 197, 1993.

O. Buchardt et al.: “Photochemical surface modification of polystyrene in the presence of cerium(IV) ammonium nitrate: improved binding of proteins, amines and mercaptans in the presence of detergent,” Biotechnol. Appl. Biochem., 17, 223, 1993.

H.I. Elsner et al.: “Use of psoralens for covalent immobilization of biomolecules in solid phase assays,” Bioconjugate Chem., 5, 463, 1994.

M. Maeda et al.: “Psoralen-containing vinyl monomer for conjugation of double-helical DNA with vinyl polymers,” Bioconjugate Chem., 5, 527, 1994.

I. Willner et al.: “Photoswitchable biomaterials: en route to optelectronic systems,” Acc. Chem. Research, 30(9), 347, 1997.

D.J. Pritchard et al.: “Simultaneous determination of follicle stimulating hormone and luteinising hormone using a multianalyte immunosensor,” Anal. Chim. Acta, 310, 251, 1995.

S.P.A. Fodor et al.: “Light-directed, Spatially Addressable Parallel Chemical Synthesis,” Science, 251, 767, 1991.

G. McGall et al.: “Light-directed synthesis of high-density oligonucleotide arrays using semiconductor photoresists,”Proc. Natl. Acad. Sci. USA, 93, 13555, 1996.

P. Morales et al.: “New method of deposition of biomolecules for bioelectronlc purposes,” Appl. Phys. Lett., 64, 1042, 1994.

G.V. Shivashankar et al.: “Biomolecular recognition using submicron laser lithography,” Appl. Phys. Lett., 73, 417, 1998.

E. Delamarche et al.: “Patterned Delivery of Immunoglobulins to Surfaces Using Microfluidic Networks,” Science, 276, 779, 1997.

G. MacBeath et al.: “Printing Proteins as Microarrays for High-Throughput Function Determination,” Science, 289, 1760, 2000.

A. Douvas et al.: “Biocompatible photolithographic process for the patterning of biomolecules,” Biosens. and Bioelectronics, 2001, in press.

International Search Report.

* cited by examiner

PHOTORESISTS PROCESSABLE UNDER BIOCOMPATIBLE CONDITIONS FOR MULTI-BIOMOLECULE PATTERNING

RELATED APPLICATIONS

This application is a National Stage entry of International Application Number PCT/GR02/00033, filed May 30, 2002, which claims priority to Greece Application 20010100271, filed May 31, 2001.

STATE OF THE ART

The photosensitive materials described in this invention are applied in the microfabrication of bioanalytical devices where biomolecules are used for molecular recognition. These types of devices are referred usually as biosensors.

Based on the molecular recognition function, the biosensors are devided in: a) biocatalytic sensors, when an enzyme recognizes an analyte generating products by catalytic reaction and b) bioaffinity sensors, which are further devided in immunosensors and DNA sensors, when an antibody recognizes an antigen-analyte and a specific part of DNA chain recognizes the complementary chain part as analyte, respectively. Due to their signal trunsduction function, the biosensors are separated in electrochemical semiconductor, piezoelectric, and optical sensors (1-2).

The patterning of many biomolecules on the same solid surface is very important in bioanalysis, because it permits the simultaneous analysis of a large number of bioanalytes precisely and with low cost; it also facilitates the processing and the transduction of the recognition signal. To achieve this goal, most of the research effort is focused on the thin film technology used in microelectronic device fabrication. However, a serious problem emerged from the transfer of this technology to bioanalytic device fabrication is the non-compatibility of photolithographic processing with the presence of biomolecules. Another serious problem for pattering e.g. proteins on solid surface is not the chemistry itself required for protein immobilization, but the whole strategy to prevent the adsorption of protein onto unwanted regions. In the following, the main methodologies that have been proposed to address these problems are presented.

Initially the biomolecules were used in photolithography to make surface patterning more convenient. Thus a denatured biomolecule layer was formed between a photoresist film and silicon dioxide layer in order to make easier the patterning of the silicon dioxide underlayer (3). Also an enzyme was dispersed in polymeric film for patterning metal by reactions depending on this enzyme (4).

The use of biomolecules in bioanalytic device fabrication was referred later. In this context it was attempted to pattern enzyme membrane photolithographically by dispersing enzyme in photopolymer solution (5, 6). The organic solvent developers, which are known to denature significantly most of the biomolecules, in combination with the application of this method only in membranes limited this method.

A positive tone photoresist was used for direct patterning of biomolecules on substrates. During this procedure selective areas of the resist film were exposed to light and removed, then biomolecules were introduced to cover these regions and finally the unexposed film was removed with acetone (7). The use of acetone for the removal of the remaining film after biomolecule deposition limited decisevely the application of this "lift-off" technique.

Also, positive photoresists were used to pattern indirectly biomolecules on substrates. According to this approach the photoresist film was photolithographically patterned, an alkylsilane covered both the substrate (exposed resist areas) and unexposed resist areas, the remaining film was stripped, an aminosilane was deposited on the regions not covered by alkylsilane and finally proteins or cells were adsorbed on the aminosilane stripes (8, 9). The whole strategy was very effective, but allowed patterning of only one type of biomolecules on substrate.

Another approach was the use of photoactivatable polymers for patterning biomolecular assemblies (10-12). More particularly, patterned network polymers were formed upon substrates and subsequently biomolecules such as antibodies or nucleic acid chains were bound on these networks. Thus, these polymers were used as photochemically activated linkers for covalent binding of biomolecules. This strategy was not general and was strictly related to the kind of biomolecules (usually antibodies) to be bound, while it remains questionable if the multi-biomolecule patterning request can be fulfilled.

A different approach was the use of e-beam or deep UV photoresists for negative and positive tone protein patterning (13). Thus, proteins were patterned on the copolymer surface via e-beam or deep UV lithography with two different mechanisms: the chemisorption- and physisorption-controlled mechanism, which gave positive and negative protein images, correspondingly. The remaining photoresist after the procedure and the obvious inability of patterning more than one proteins on the same substrate limited the application of this method. Other propositions have been reported using e-beam lithography with photoresist in biodevice fabrication, but with potential patterning of a single kind of biomolecules, due to high temperature thermal treatment and organic solvent development preceded the biomolecule deposition (14).

Furthermore, several methods of photochemical surface modification for biomolecule patterning without using photoresists have been reported. Characteristic category is the photochemical modification of organosilane self-assembled monolayers (SAMs) for the formation of coplanar molecular assemblies, which are susceptible to selective biomolecule immobilization in micro scale (15-19). A similar approach is the photochemical modification of polymer surface using cerium(IV) ammonium nitrate or psoralens for covalent immobilization of biomolecules (20, 21). A slightly different, but more complicated method is the intercalative binding of psoralen moiety into DNA double strands, the light-induced DNA strands crosslinking through this moiety and then copolymerization of the resulting DNA bearing vinyl groups with a comonomer introduced (22).

The use of photoisomerizable antigen monolayers for patterning antibodies on surfaces (23) and the light-induced protein immobilization on avidin-photobiotin layer (24) are very interesting strategies, though not general. An exceptional methodology for oligonucleotide arrays formation was the light-directed, spatially localized peptide synthesis on solid phase (25). Concurrently the use of high-resolution imaging photoresist in combination with the light-directed oligonucleotide synthesis was resulted in significant increase of oligonucleotide arrays density (26).

The laser induced plasma vaporization and ionization technique was proposed for electric field assisted deposition of proteins (27), but the ionization of proteins is itself a limitation factor for the method. Also the protein patterning on gold-coated glass substrate through laser lithography was reported (28), while it is unknown if the biomolecule functionality was not affected by the extremely hot, ablated, gold region.

A different approach for protein micropatterning was recently reported by attaching proteins through chemical reactions within elastomeric microfluidic networks (29). Also the micropatterning of different proteins was achieved using a high-precision robot for the delivery of nanoliter protein solution volumes onto chemically modified glass slides followed by covalent binding of proteins on these spots (30).

Short Presentation of the Invention

A different approach of the above mentioned is presented in this invention: a chemically amplified photoresist based on the copolymer consisted of the following monomers: 2-hydroxyethyl-methacrylate, isobornyl-methacrylate, t-butyl-methacrylate and acrylic acid (FIG. 1) is photolithographically processed under biocompatible conditions for micropatterning more than one proteins on solid substrate. The whole strategy is a version of the "lift-off" lithography used in microelectronics, but fulfills the severe biocompatible requirements successfully, due to the chemically amplified photoresist based on the invented copolymer. The current methodology (the lithographic process and the photoresist) is a continuation of our research effort previously reported, in which a similar photolithographic lift-off technique was followed, using, however, a different chemically amplified photoresist based on the homopolymer t-butyl-acrylate (31, 32).

It is an object of this invention to micropattern one or more proteins on a substrate.

It is also an object of this invention to use the photolithographic "lift-off" technique in biocompatible conditions to micropattern one or more proteins on a substrate.

It is still an object of this invention to make a copolymer based photoresist, which can be processed with the biocompatible photolithographic "lift-off" technique to micropattern one or more proteins on a substrate.

It is also another object of this invention to make a copolymer based photoresist, which can be processed with the biocompatible photolithographic "lift-off" technique to micropattern one or more proteins having resolution on the order of 1 to 100 microns on aminosilane-treated silicon surface.

It is still another object of this invention to make a copolymer-based photoresist, which can be processed with the biocompatible photolithographic "lift-off" technique to define one or more protein "bands" (parallel zones of proteins) on the internal surface of polystyrene or poly(methyl-pentene) capillary tube.

The above objects—except of the last object—are accomplished by the general lithographic scheme that describes patterning of two proteins on silicon surface treated with 3-aminopropyl-triethoxy-silane (APTES) in the following steps (FIG. 2):

(1) Coating of the photoresist on the APTES-treated silicon surface and subsequent thermal treatment of the film;

(2) Exposure of selected photoresist areas at specific wavelength radiation;

(3) Dissolution of the previously exposed photoresist areas with dilute aqueous base;

(4) Deposition of the active protein, which is adsorbed on the substrate areas uncovered with the photolithographic steps (2) and (3), and possibly on the unexposed film areas;

(5) Exposure at the same wavelength radiation of the remaining photoresist film;

(6) Dissolution of the previously exposed remaining photoresist by dilute aqueous base;

(7) Deposition of the inert protein, which is adsorbed on the substrate areas uncovered with the lithographic steps (5) and (6), and on the free binding sites of the areas where the active protein was adsorbed.

Thus, two different proteins are patterned on the APTES-treated silicon surface: the active protein is patterned on the substrate areas where the initially exposed photoresist regions were located, and the inert protein is patterned on the other surface areas. (The inert protein is a protein that does not interact with the fluorescent-labeled antibody, which is added to react with the patterned active protein after the whole lithographic process for the visualization of the protein microstructure). The steps that follow the deposition of the active protein molecules do not affect their immunoreactivity and are available for subsequent binding with their antibody molecules.

A slight modification of the previous lithographic scheme, which would permit micropatterning of three different proteins on APTES-treated silicon surface and accomplish the same objects, is the process comprising the following steps (FIG. 3):

(1) Coating of the photoresist on the APTES-treated silicon surface and thermal treatment of the film;

(2) Exposure of selected photoresist areas at specific wavelength radiation;

(3) Dissolution of the exposed areas with dilute aqueous base;

(4) Deposition of the first active protein, which is adsorbed on the substrate areas uncovered with the photolithographic steps (2) and (3), and possibly on the unexposed film areas;

(5) Deposition of the inert protein which is adsorbed on the free binding sites of the substrate, and possibly on the unexposed film areas;

(6) Exposure of other film areas at the same wavelength radiation;

(7) Dissolution of the previously exposed film areas by dilute aqueous base;

(8) Deposition of the second active protein, which is adsorbed on the substrate areas uncovered with the photolithographic steps (6) and (7), and possibly on the unexposed film areas;

(9) Exposure at the same wavelength radiation of the remaining photoresist film;

(10) Dissolution of the previously exposed remaining film by dilute aqueous base;

(11) Deposition of the inert protein, which is adsorbed on the substrate areas uncovered with the lithographic steps (9) and (10), and also on the free binding sites of the areas where the two active proteins were adsorbed.

Thus, three different proteins are patterned on the APTES-treated silicon surface: the two active proteins are adsorbed on the substrate areas where the twice-selected exposed regions were located, and the inert protein is adsorbed on the other surface areas. Also the steps that follow the deposition of the two active protein molecules do not affect their binding functionality. Modifying slightly the previous lithographic scheme four, five, etc. different proteins can be patterned on silicon surface without affecting their immunoreactivity.

The lithographic scheme that accomplishes the last object, thus, allowing the definition of protein "bands" on a plastic capillary inner surface is: the first of the two preceeding schemes if "bands" of two different proteins have to be defined (FIG. 4), the second of the two preceeding schemes if three proteins have to be defined, and so on. The difference now is the way that the process steps are carried out (e.g.

introduction of the photoresist, the aqueous base or the protein solution with a syringe, the action of the capillary walls as radiation cut-off filter, etc).

BRIEF DESCRIPTION OF THE INVENTION FIGURES

FIG. 1. The chemical structure of the (meth)acrylate copolymer invented, which allow the photoresist to be photolithographically processed in biocompatible conditions.

Figure 2:
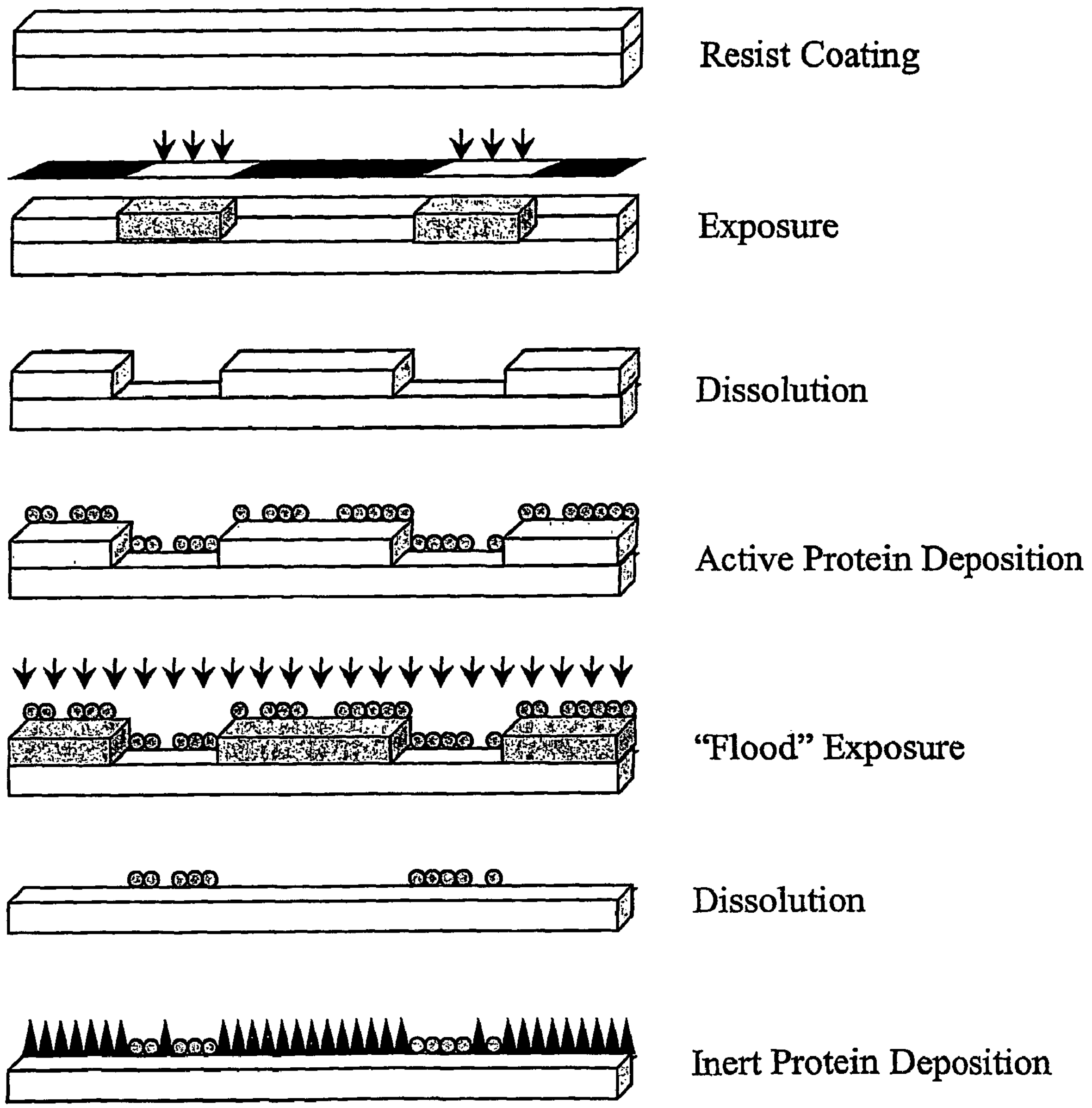

FIG. 2. The lithographic scheme for patterning two different proteins on APTES-treated silicon surface with the biocompatible photolithographic processing (lift-off) of the (meth)acrylate photoresist.

Figure 3:
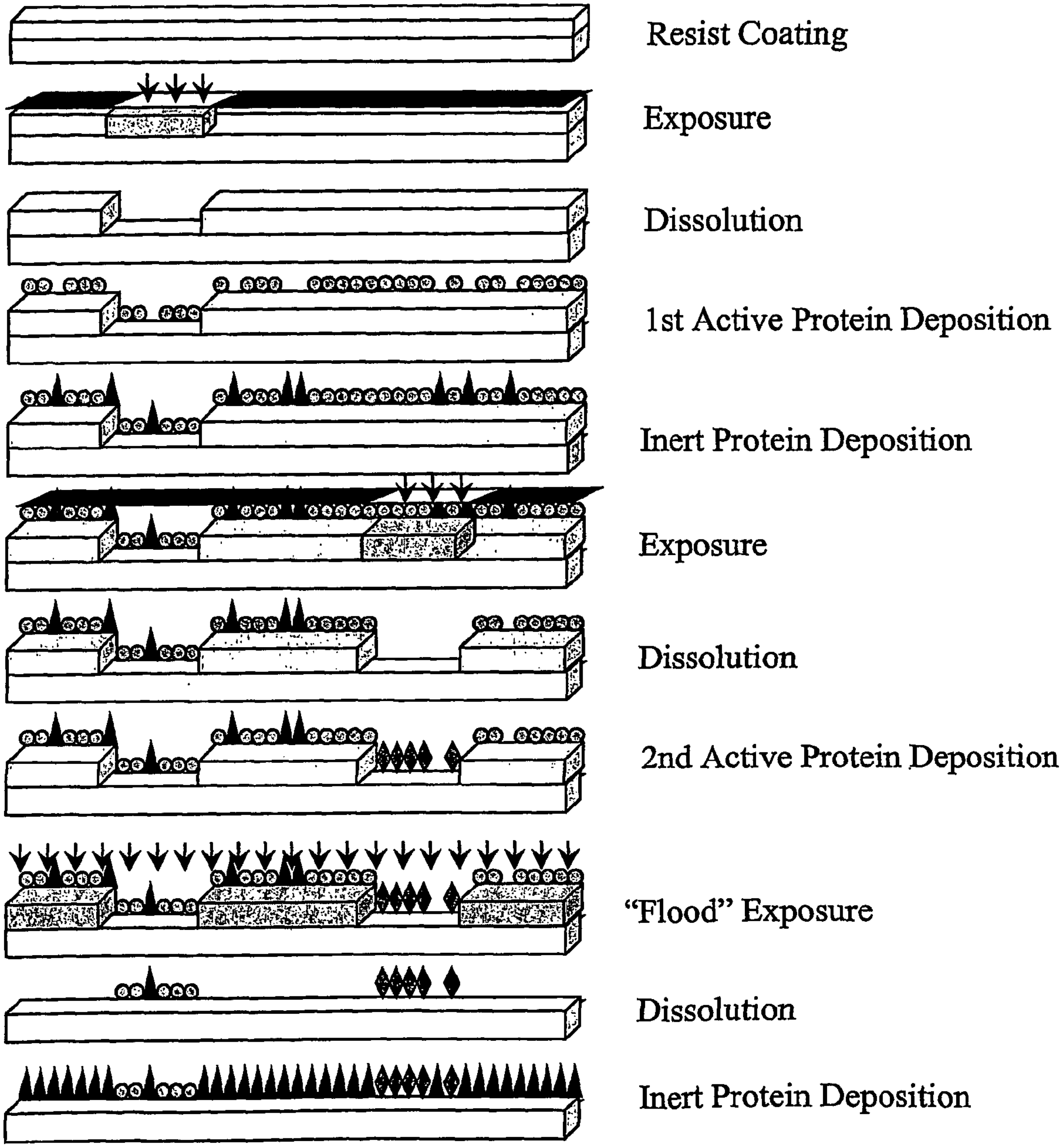

FIG. 3. The lithographic scheme for patterning three different proteins on APTES-treated silicon surface with the biocompatible photolithographic processing (lift-off) of the (meth)acrylate photoresist.

Figure 4:
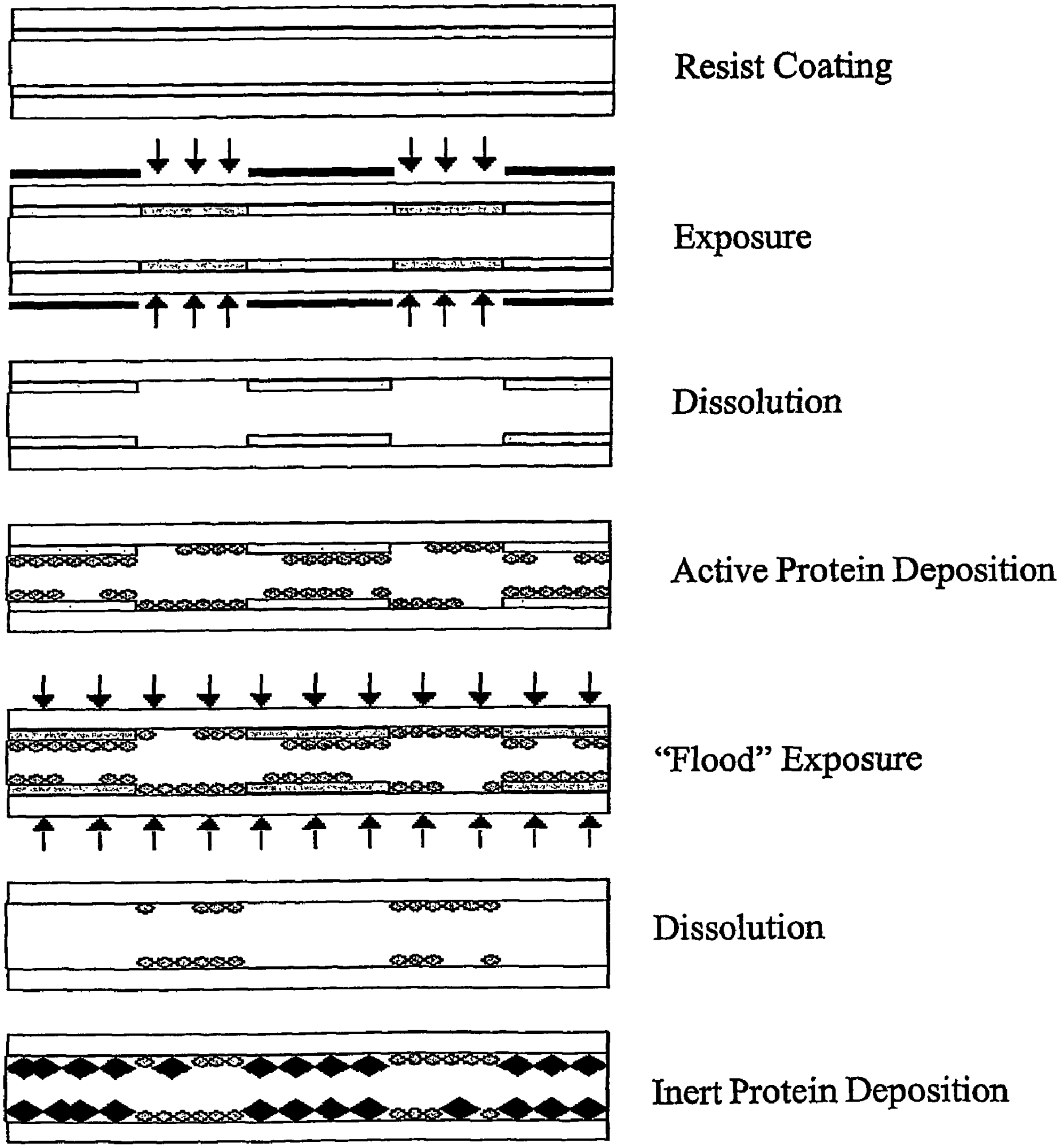

FIG. 4. The lithographic scheme for the definition of two protein "bands" on capillary inner surface with the biocompatible photolithographic processing (lift-off) of the (meth) acrylate photoresist.

Figure 5:
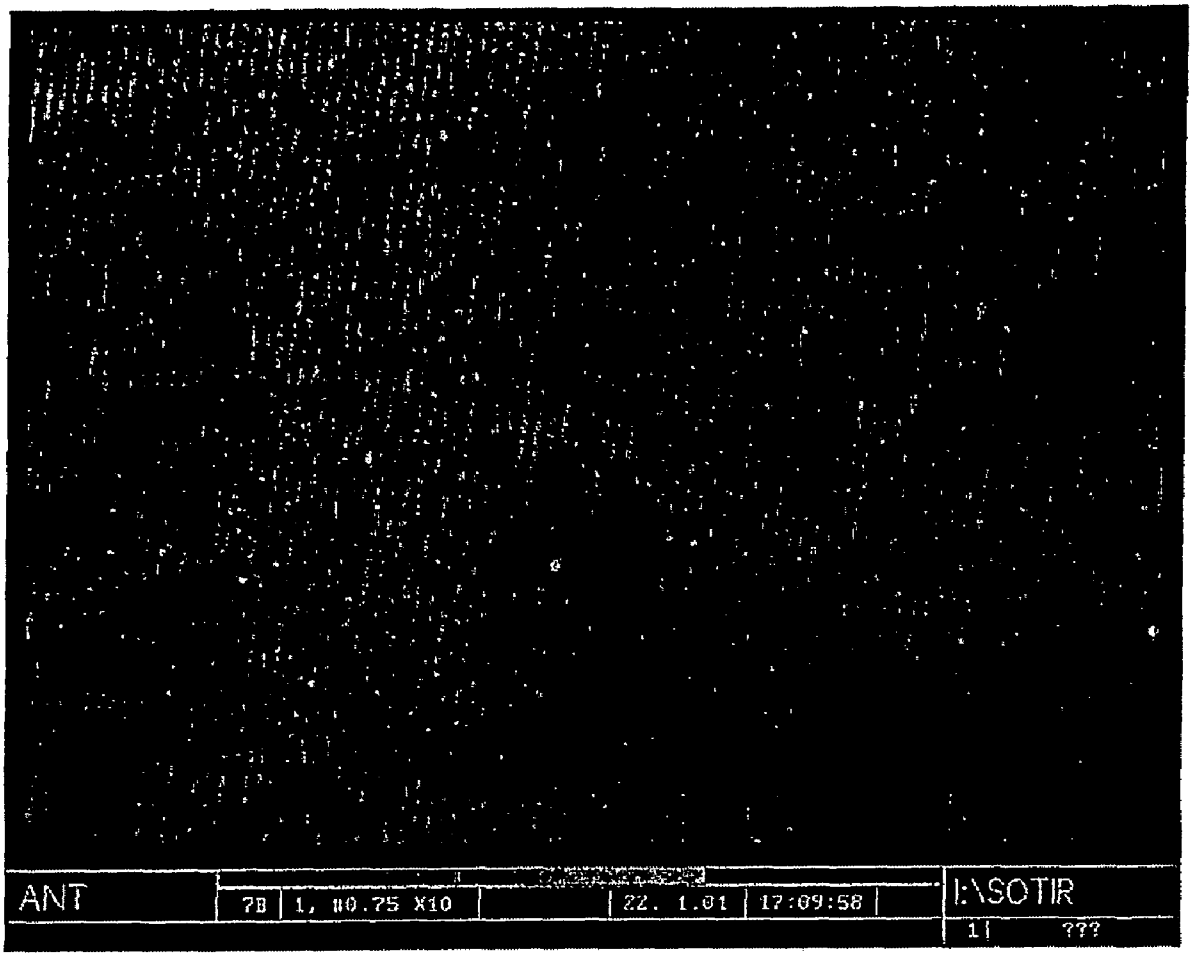

FIG. 5. Microstructures of 3.75 μm lines/spaces of two different proteins: rabbit-IgG (green lines—active protein) and bovine serum albumin (black lines—inert protein) obtained by the biocompatible photolithographic processing of the (meth)acrylate photoresist on APTES-treated silicon surface.

Figure 6:
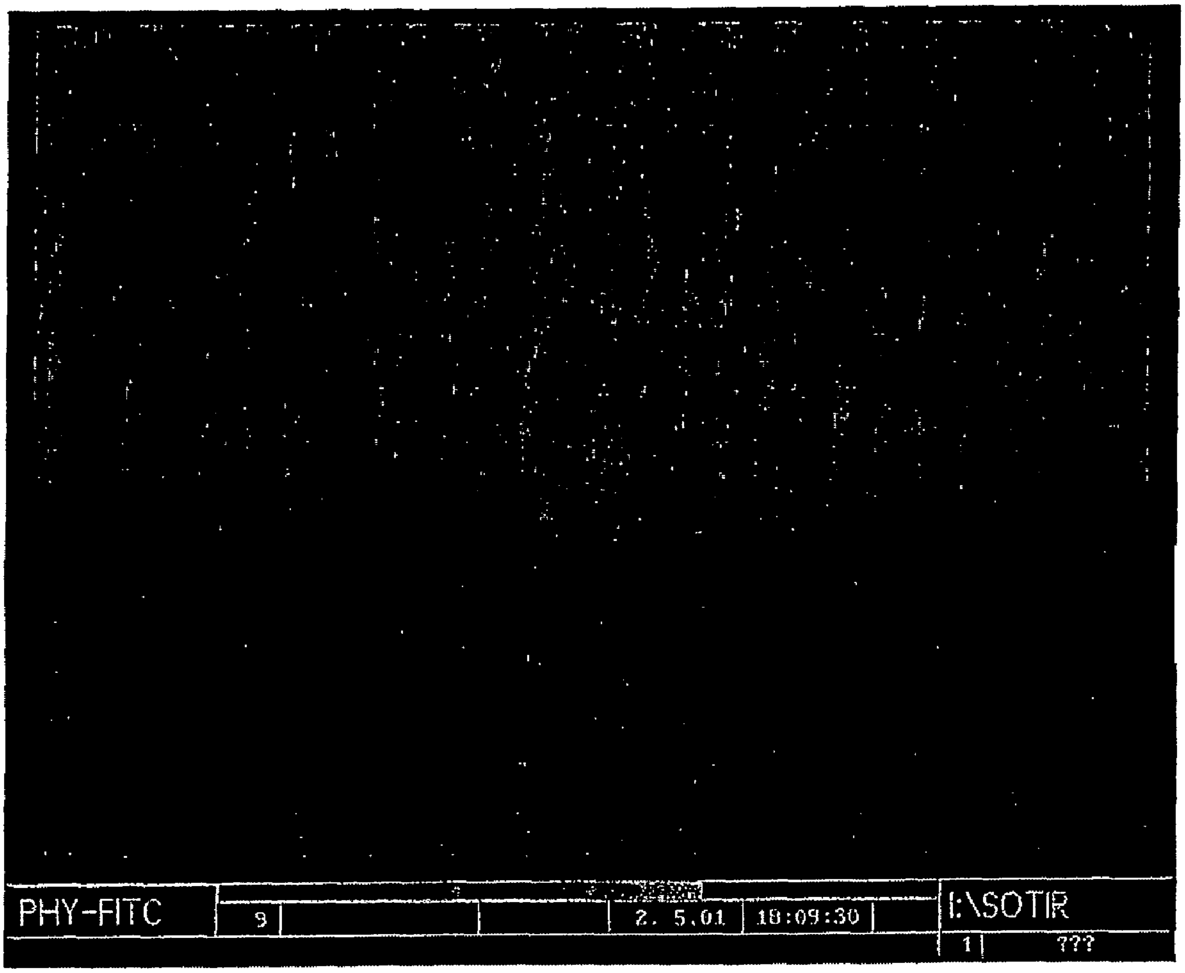

FIG. 6. Microstructures of 22.5 μm lines/spaces of three different proteins: mouse-IgG green lines—first active protein), biotinylated bovine serum albumin (red lines—second active protein) and bovine serum albumin (black lines—inert protein) resulted by the biocompatible photolithographic processing of the (meth)acrylate photoresist onto APTES-treated silicon surface.

Figure 7:
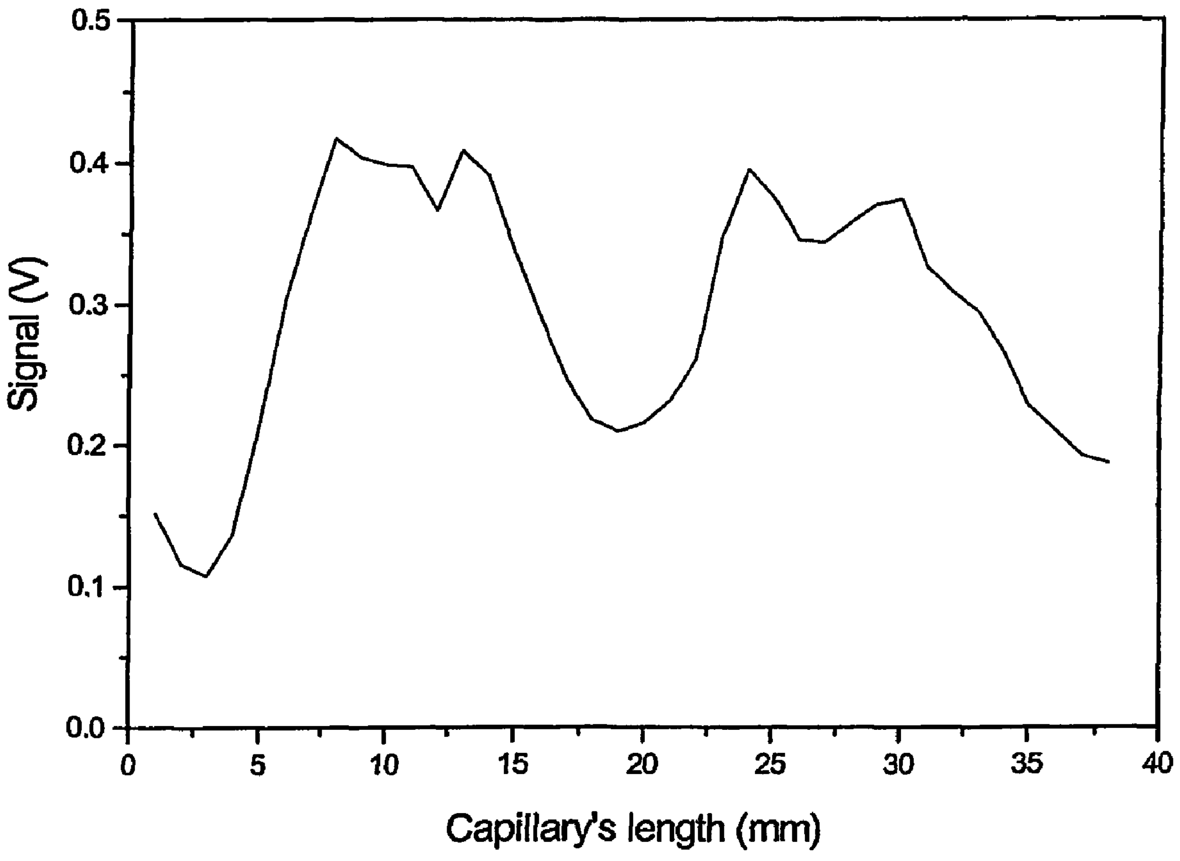

FIG. 7 Two rabbit-IgG (active protein) "bands" defined among bovine serum albumin (inert protein) areas on poly (methyl-pentene) capillary inner surface by the biocompatible photolithographic processing of the (meth)acrylate photoresist. The two protein "bands" are visualized by introduction of anti-rabbit-FITC conjugate and subsequent fluorescence scanning of the whole capillary showing two distinct signals.

DETAILED DESCRIPTION OF THE INVENTION

In the first photolithographic scheme (FIG. 2) two proteins can be patterned on silicon surface. Initially the silicon wafer surface is treated with 3-aminopropyl-triethoxy-silane (APTES) in order to become hydrophobic for the subsequent physisorption of proteins. Then, the photoresist solution is used for the creation of the photoresist film onto the treated silicon surface. The photoresist solution constists of two compounds in an appropriate solvent: one component is the copolymer invented and the other is a triphenyl or triaryl sulfonium salt acted as photosensitiser. This solution is casted onto the treated silicon wafer surface and then the wafer is spinned in order to form a homogenic thickness film. Thermal treatment is followed for the vaporization of the solvent remained in the polymer matrix and the rearrangement of the polymer chains. Although thermal treatment is not appropriate, usually it takes place for the formation of a high quality polymer film.

In the second step defined areas of the polymer film are exposed to radiation via a two-dimension photolithographic mask: a mask with a transparent pattern on its surface, which is transferred to the resist film. This mask must be kept in contact to the film (contact printing) to prevent phenomena of light diffraction, which would generate unwanted exposed areas. Also the radiation wavelength is selected in order to control effectively the photo-induced reactions (the radiation wavelength must be in the photosensitiser absorption region). Thus, radiation band filters or cut-off filters are placed over the mask for the selection of deep UV or near UV radiation region, respectively. For the chemically amplified resist as the current one, a thermal treatment step usually takes place after the exposure. But this photoresist, due to the (meth)acrylate copolymer invented, does not need to be postexposure treated and this is one of the main differences with our previously introduced biocompatible photoresist (31, 32).

The third step is the removal of the previously exposed resist areas using a very dilute aqueous base, which can be tolerated by the proteins. More particularly we had reported formerly (31,32) that the aqueous base solutions of 0.27 N tetramethyl ammonium hydroxide (TMAH concentration (standard aqueous base developers used in semiconductor technology) denature almost completely the proteins, while the 100 times diluted of this aqueous base solution ($2.7\times10^3$ N TMAH concentration) generates less than 10% decline of their immunoreactivity; this was considered by us as a limit of protein denaturation and so this base concentration was the maximum value used. Actually the exposed areas of the current (meth)acrylate based photoresist can be dissolved in even more diluted aqueous base in comparison with our previous biocompatible photoresist (31, 32).

In the fourth step the patterned resist film is covered with the active protein solution for the adsorption of this protein on the substrate. Actually the protein is physisorbed not only on the substrate areas, where the photoresist areas were previously exposed and removed, but also onto the remained unexposed film regions. The last one must not be considered as an inefficiency of the process, because the unexposed resist areas along with the protein monolayer adsorbed on them will be exposed and removed in the following steps. In this process the proteins are adsorbed on the hydrophobic substrate, but it would be the same if the proteins were covalently bound on the surface without any changes in the lithographic process. In addition it would cause no changes to the process sequence and conditions if other biomolecules were used instead of proteins, such as enzymes, nucleic acid chain parts, etc.

The fifth step is consisted in the "flood" exposure of both the remained photoresist film and substrate areas where the proteins have been adsorbed. The "flood" exposure is carried out without using a mask, because the whole film must be exposed, and not specific regions. The radiation wavelength is the same with that in the previous exposure and is selected again using band filters or cut-off filters. It is necessary for this step that the radiation used must not affect the adsorbed proteins, because in the "flood" exposure they are irradiated together with the remained photoresist. Thus, radiation in near UV or visible is preferred with nearly no limitation in exposure time, while exposure duration in deep UV region must be kept relatively small. In addition the duration of the second exposure is usually increased in comparison with the first one, because a small part of the photoresist surface is deactivated in a way by the preceded covering of the film with the protein solution; a surface dissolution of the film's photosensitiser is a possible explanation to this phenomenon. As with the second step no thermal treatment is needed after the photoresist exposure, again because of the incomparable dissolutive convenience of the exposed areas of our photoresist.

In the sixth step the dissolution of the previously exposed resist areas is taken place. The TMAH concentration of the aqueous base solution that is used in this step may be slightly increased in comparison with the first dissolution made (third step), but it remains sufficiently below the base concentration level that is not tolerated by the proteins. At the end of this step a pattern of protein molecules is created on the substrate regions where the initially exposed resist areas (in the second step) were located.

In the seventh step the surface is covered by an inert protein solution. Therefore the inert protein molecules are adsorbed physically onto all free surface binding sites: not only on the binding sites of the substrate regions uncovered with lithography in steps (5) and (6), but also on the free binding sites that were not covered by the active protein molecules. The reason is to prevent non specific binding of the analyte: the analyte (antibody) must be bound only onto the active protein (antigen) patterned and not adsorbed on the surface, in order to confer the concentration of the analyte (use of the device in immunoassay format). At the end of this step and of the whole process two proteins are patterned on the APTES-treated silicon surface: an active protein that can be recognized by its antibody and an inert protein that does not interact with this antibody. This pattern can be visualized by the covering of the surface with the appropriate solution containing the antibody labeled with a fluorescence substance and consequently identification of the immunocomplex in an epifluorescence microscope (Example 1).

The process that allows the patterning of three proteins is the same with that of patterning two proteins in relation to the general idea: the biocompatible photolithography of the (meth)acrylate based photoresist. The processing conditions of each step may have been altered and even the sequence of the steps, but this does not reduce the biocompatibility and the effectiveness of the method. About the differentiation of the process steps sequence, it concerns only the "blocking" steps that is the steps whose purpose is to introduce molecules of an inert protein in order to occupy any uncovered substrate sites. This step is taken place once at the end of the process, when two proteins have to be patterned. Now for the process of patterning three proteins the "blocking" step is taken place twice, not necessarily in the same conditions: once immediately after the deposition of the first active protein and then again at the end of the process. Similarly if four proteins have to be patterned the "blocking" step must take place three times: firstly immediately after the deposition of the first active protein, secondly after the deposition of the second active protein and then again at the end of the process.

About the change of the process conditions, if the number of proteins that have to be patterned is increased this alteration is necessary for the effective removal of the resist film. The adsorption of the proteins onto the substrate is achieved, when the patterned photoresist is immersed in slightly base solutions of proteins for a considerable time. Although these solutions are more diluted basic solutions than those used after every film exposure, they affect the resist film significantly, because they cover it for a long time (may be more than an hour is necessary). This causes deactivation of the polymer film surface layer and subsequent decrease in photoresist sensitivity, because of possible dissolution of the photoacid generator there, as it was previously mentioned. Also the unwanted slightly exposed photoresist areas are more deactivated by the protein adsorption. That is why the limitation of the light diffraction and consequently the exposure of the unwanted regions is an essential matter to the current photolithographic approach. The radiation absorption by the protein monolayer physisorbed on the resist film must not contribute significantly to the polymer film surface deactivation, because the thickness of the protein monolayer is extremely small (in the order of 10 A) and consequently its absorption is very small in comparison to the resist film.

To address the problem of surface deactivation of the polymer film that is its sensitivity decline, less mild-though biocompatible-process conditions must be used for the removal of the film. Thus higher exposure duration is needed and/or slightly more concentrated base solutions for the development of the film; usually it is preferred the first one and only if it is inevitable the second one. Consequently for the three-protein patterning process the first exposure time might be smaller than the second one and the second one smaller than the third one. Similarly the first aqueous developer solution might have smaller base (TMAH) concentration than the second one, the second one smaller than the third one and the third one less to the one tolerated by the proteins (only 10% of immunoreactivity reduction is accepted; see above).

The three-protein pattern on the APTES-treated silicon substrate can be visualized by two alternative ways: a) introduction of an appropriate solution containing both antibodies of the two active proteins at the end of the photolithographic process or b) introduction of the two antibodies separately: at first deposition of the first active protein-antibody after the corresponding "blocking" step (step 5) and then deposition of the second active protein-antibody after the second "blocking" step (step 11). In both ways the antibodies are labeled with a different fluorescent substance so that each immunocomplex formed can be identified in the epifluorescence microscope. Usually it is preferred the first way of the above in order to avoid the effect of the antibody solution on polymer film, but this depends on the antibodies too, e.g. if they can bind their corresponding antigens in the same pH solution, etc (Example 2).

When the biocompatible photolithographic process is applied for the patterning of e.g. two proteins onto the plastic capillary internal surface, extra limitations have been arisen, except the biocompatible one. The solvent of the copolymer-based photoresist must not influence the plastic material of the capillary tube, which is usually polystyrene, poly(methyl pentene), poly(methyl methacrylate), etc. Also the capillary walls act as cut-off filters and allow passing only radiation in near UV or visible region; consequently the photoresist film should be sensitive to this radiation region. The last requirement posed by the cylindrical geometry of the substrate forces us to use the appropriate photosensitisers, a problem that is not faced to the silicon substrate where deep UV exposure could be used, but in low doses in order not to denature the patterned proteins.

Moreover practical problems concerning the application itself of the photolithographic process are efficiently overcome. Thus the photoresist solution is introduced in the capillary using a syringe, it is left in the horizontal position for 1-2 min and then it is extracted by turning the tube in the perpendicular position. The photoresist film formed can be thermally treated by introduction of the capillary into aluminum plate holes of similar size with the capillary. After that, specific areas of the capillary external surface are exposed and the other areas are covered with a non-transparent tape; the use of radiation filters is not necessary, since the capillary walls act as cut-off filters. Also for the homogeneous exposure of the photoresist film the capillary is turned by 60° around its axis at the end of each irradiation and consequently the tube is turned five times in order to achieve irradiation of the whole film. Then the dissolution of the irradiated resist areas is taken place by introducing the dilute aqueous base solution with a syringe repeatedly (at least twice from both capillary ends in order to ensure that fresh developer solution is continuously added). In a following step the protein solution is added, incubated for the necessary period, and then rinsed. Afterwards, the whole resist film is irradiated with the preceding homogeneous way (turning the capillary by 60° after each exposure). Then the dilute aqueous base is introduced into the capillary by a syringe (see above). Finally, the inert protein solution is introduced into the tube and incubated for a certain period of time. For the visualization of the two protein locations onto the capillary inner surface the specific antibody labeled with a fluorescent substance is introduced into the capillary and subsequent fluorescence scanning of the tube is taken place by an optical set-up constructed in our laboratory. Thus the locations containing the immunocomplex formed are indicated by different signals (Example 3).

The current photoresist is based on the copolymer: 2-hydroxy-ethyl-methacrylate, isobornyl-methacrylate, t-butyl-methacrylate and acrylic acid. The chemical behavior of the resist is the same with the previously introduced photoresist based on the homopolymer t-butyl acrylate. The reaction mechanism is the chemical amplification mechanism, in which the acid generated by the photosensitizer during the exposure acts as a catalyst for the subsequent dissociation of the ester groups of the copolymer components in a way that for every ester pendant group that is broken with the aid of acid a new acid is generated. From the dissociation of the ester group methacrylic acid is generated, which is soluble by diluted aqueous base solutions. The extension of the ester groups dissociation defines the following dissolution of the exposed photoresist areas. The difference between this photoresist and our previous one (31, 32) is that now the dissolution of the exposed photoresist areas can be achieved without thermal treatment of the polymer film. The photosensitizers used are mainly two: a) triphenyl sulfonium hexafluoroantinonate for the irradiation at deep UV (254 nm) or b) a 50% w/w solution in propylene carbonate of a 1:1 mixture of two triarylsulfonium hexafluoroantimonate salts (one having diphenylthioether as an aryl substituent and the other is a thiodimer of triphenyl sulfonium hexafluoroantimonate salt), for exposure at near UV ($\lambda$>300 nm).

The whole photolithographic strategy invented (both the copolymer-based photoresist and the biocompatible photolithographic "lift-off" technique) is a unique method for patterning biomolecules on solid surface. It is a general methodology independent of the biomolecules that have to be patterned: proteins, enzymes or oligonucleotides can be similarly patterned. Furthermore it is independent of the substrate material and geometry: it can be applied on silicon or polymeric substrate, in planar or cylindrical surface. Moreover, whatever way the biomolecules are bound onto the substrate—adsorbed or covalently bound—it is equally functional. No expensive or complicated instruments are needed; just the photoresist and the usual irradiation sources used in deep UV or near UV exposure. And finally it can pattern in micro scale easily more than one biomolecules on the same substrate. In relation to our former invented photolithographic strategy (31) the main differences are summarized to the following: a) the photoresist is based now on the copolymer synthesized by us consisted of 2-hydroxyethyl-methacrylate, isobornyl-methacrylate, t-butyl-methacrylate and acrylic acid in a 30/40/20/10 weight ratio, while the previous one was based on the homopolymer t-butyl acrylate, b) the photolithographic process fulfills better the biocompatibility requirements since using the copolymer synthesized lower exposure times are necessary, no thermal treatment is needed after the exposure and even more diluted aqueous bases can be used for the removal of the exposed photoresist areas. To show the effectiveness of this methodology some characteristic examples are presented. In examples 1 and 2 microstructures of two and three different proteins photolithographically patterned on APTES-treated silicon substrate are shown, correspondingly. In example 3 two "bands" of proteins photolithographically defined on the capillary inner surface are presented.

EXAMPLES

Example 1

Initially the silicon wafer surface is treated with 3-amino-propyl-triethoxysilane (APTES) solution in order to make it hydrophobic (amino groups are formed) and susceptible to physical binding by the proteins. Thus a clean silicon wafer is immersed in a "pyranha" solution, for 1 hr, in ambient temperature; this solution is a 1:1 mixture of 31% v/v $H_2O_2$ aqueous solution and 97% v/v $H_2SO_4$ aqueous solution. Then the wafer is washed very well with deionized water and it is immersed in a bath with continuously refreshing deionized water (until its special resistance take the value of 12 M$\Omega$). The water is removed from the wafer surface under a nitrogen stream. Afterwards, it is immersed in 2% v/v APTES aqueous solution for 20 min and is quickly immersed and taken out from a bath with fresh deionized water, and dried under a nitrogen stream; the reason that the wafer surface is immersed now in deionized water is to rinse it from the aminosilane salts that are not bound to the surface. Subsequently the wafer is thermally treated at 120° C. for 20 min. Finally it is immersed in deionized water in ultrasonic bath for 5 min, dried under a nitrogen stream and thermally treated at 95° C. for 5 min (in order to remove completely the water from the surface).

The photoresist solution is prepared as following: A 10% w/w solution in ethyl lactate, of our synthesized copolymer consisted of 2-hydroxyethyl-methacrylate, isobornyl-methacrylate, t-butyl-methacrylate and acrylic acid in a 30/40/20/10 weight ratio, is formulated. The solution is stirred at least for 1 hr with parallel mild thermal treatment (50° C.). Then triphenylsulfonium hexafluoroantimonate salt, provided by General Electric, is added as photosensitizer, so that the final concentration of the salt to be 10% w/w in solids. The final solution is stirred for ½ hr and after that filtered (with filters of 0.2 μm pore size).

To pattern two proteins—an active and an inert protein—onto the treated silicon surface the first photolithographic process is followed (FIG. 2). Thus the above photoresist solution is cast on the center of the treated silicon wafer covering about the ¾ of its surface. The lithographic resist is coated on the whole silicon surface by spinning the wafer at 3000 rpm for 30 sec. The coated wafer is baked in an oven at 70° C. for 5 min. Selected areas from the resist film are exposed with an Oriel Hg—Xe 500 W (operated at 450 W) radiation source. The selection of the resist areas that are going to be patterned is done with a quartz mask, which is placed over the polymer film and in contact with it (through vacuum) for preventing light diffraction. The selection of the wavelength radiation 254 nm (deep UV) is made with a broadband filter (50 nm bandwidth at half maximum), which is placed over the mask. The exposure dose is 36 $mJ/cm^2$. Subsequently the exposed areas are dissolved by immersion of the photoresist film in a $1.35\times10^{-3}$ N aqueous solution of tetramethyl ammonium hydroxide (TMAH for 2 min, washed with deionized water and dried under a nitrogen stream. Then the wafer surface is covered with a 20 mg/L rabbit IgG solution in 0.04 M phosphate buffer, pH 6.5, for 30 min. After that the surface is washed with deionized water and dried under a nitrogen stream. Subsequently the whole surface is exposed ("flood" exposure) using the same exposure tool and filter (254 nm broadband filter); the exposure dose is now 109 $mJ/cm^2$. The remained film areas are dissolved by immersion of the photoresist in a $2.7\times10^{-3}$N TMAH aqueous solution for 2 min, washed with deionized water and dried under a nitrogen stream. Finally the whole surface is covered with a 10 g/L bovine serum albumin solution in 0.1 M $NaHCO_3$ buffer, pH 8.5, for 1 hr and dried with nitrogen stream. At the end of the process two proteins are patterned onto the APTES-treated silicon surface: rabbit IgG (active protein) and bovine serum albumin (inert protein).

To visualize the created protein pattern the substrate is immersed in a 20 mg/L goat anti-rabbit IgG-fluorescein isothiocyanate conjugate solution in 0.15 M Tris-HCl buffer, pH 8.25, containing 1 g/L bovine serum albumin, 0.5 g/L bovine IgG, 1 M KCl and 0.2 g/L ethylmercury-thiosalicylic acid sodium salt, and incubated for 3 days, at 4° C. Then the substrate is taken out, washed with a 0.01 M Tris-HCl buffer, pH 8.25, containing 0.05% (v/v) Tween 20, and observed in epifluorescence microscope. Microstructures of 3.75 μM lines/spaces of two proteins: rabbit-IgG (green lines) and bovine serum albumin (black lines) are obtained (FIG. 5).

Example 2

In the beginning the silicon wafer surface is treated with 3-aminopropyl-triethoxysilane (APTES) as it is described in Example 1. After that the photoresist solution is prepared. A 10% w/w solution in ethyl lactate, of our synthesized copolymer consisted of 2-hydroxyethyl-methacrylate, isobornyl-methacrylate, t-butyl-methacrylate and acrylic acid in a 30/40/20/10 weight ratio, is formulated. The solution is stirred at least for 1 hr with parallel mild thermal treatment (~50° C.). Then a 50% w/w solution in propylene carbonate of a 1:1 mixture of two triarylsulfonium hexafluoroantimonate salts (one having diphenylthioether as an aryl substituent and the other is a thiodimer of triphenyl sulfonium hexafluoroantimonate salt), provided by Union Carbide with the name UVI 6974, is added to the copolymer solution, so that the final concentration of the two salts totally to be 30% w/w in solids. The ultimate solution is stirred for 30 min and then filtered (with filters of 0.2 μm pore size).

The second photolithographic process (FIG. 3) is followed, because three different proteins (two active and one inert) are going to be patterned. Thus the photoresist film is coated on the treated silicon wafer by spinning it at 3000 rpm for 30 sec. The film is baked in an oven at 95° C. for 5 min. The film areas that have to be exposed are selected by placing a quartz mask over the film and in contact (through vacuum) with it. Also the required radiation region for λ>300 nm (near UV) is done by using a pyrex cut-off filter over the mask. The exposure tool used is a Karl Suss aligner and the irradiation time is 5 min. Then the exposed areas are developed by immersion of the wafer in a $1.35\times10^{-3}$ N aqueous solution of tetramethyl ammonium hydroxide (TMAH) for 2 min, washing with deionized water and drying under a nitrogen stream. Afterwards, the surface is covered with a 50 mg/L mouse IgG solution in 0.04 M phosphate buffer, pH 6.5, for 30 min; it is washed with deionized water and dried under a nitrogen stream. Then it is covered with a 10 g/L bovine serum albumin solution in 0.04 M phosphate buffer, pH 6.5, for 55 min, washed with deionized water and dried under a nitrogen stream. Areas of the patterned film are selected for exposure by covering some of the unexposed areas and leaving others to irradiation, but always using the pyrex cut-off filter. The exposure lasts again 5 min. The exposed areas are removed by immersion of the wafer in a $2.7\times10^{-3}$ N aqueous TMAH solution for 1 min; the substrate is washed with deionized water and dried under a nitrogen stream. After that the surface is covered with a 20 mg/L biotinylated-bovine serum albumin solution in 0.04 M phosphate buffer, pH 6.5, for 45 min; it is washed with deionized water and dried under a nitrogen stream. Accordingly the whole surface is exposed ("flood" exposure) for 10 min with the pyrex filter. It is immersed in a $2.7\times10^{13}$ N aqueous TMAH solution for 5 min, rinsed with deionized water and dried under a nitrogen stream. Thus, all the remained photoresist areas are dissolved. Finally the silicon surface is covered with a 10 g/L bovine serum albumin solution in 0.1 M $NaHCO_3$ buffer, pH 8.5, for 2 hr, washed with deionized water and dried with nitrogen stream. At the end of the photolithographic process three proteins are patterned on the APTES-treated silicon surface: mouse IgG (first active protein), biotinylated-bovine serum albumin (second active protein) and bovine serum albumin (inert protein).

The protein pattern is visualized by incubation of the wafer in a solution of 20 mg/L goat anti-mouse IgG-fluorescein isothiocyanate conjugate and 5 mg/L streptavidin-R-phycoerytirin conjugate in 0.15 M Tris-HCl buffer, pH 8.25, containing 5 g/L bovine serum albumin, 0.5 g/L bovine IgG, for 2 days, at 4° C. After that the substrate is taken out, washed with a 0.01 M Tris-HCl buffer, pH 8.25, containing 0.05% (v/v) Tween 20 and observed using epifluorescence microscope. Microstructures of 22.5 μm lines/spaces of three different proteins: mouse-IgG (green lines), biotinylated bovine serum albumin (red lines) and bovine serum albumin (black lines) are obtained (FIG. 6).

Example 3

For the definition of protein "bands" onto the internal surface of a plastic capillary tube the third biocompatible photolithographic process (FIG. 4) is used. The characteristics of the capillary, which is used in immunoanalysis are the following: 6 cm length, 1 mm internal diameter and 1 mm walls thickness; the material is poly(methyl pentene). The photoresist solution used is the same with the Example 2: a 10% (w/w) solution of our synthesized copolymer in ethyl lactate with 30% (w/w in solids) of the 1:1 mixture of the two triarylsulfonium hexafluoantimonate salts named UVI 6974.

Thus, the photoresist solution is introduced by a syringe into the capillary, is left horizontally for 2 min and then is extracted by turning the capillary perpendicularly. The photoresist film formed has a medium thickness of ~3 μm; a gentle nitrogen stream is used to remove the solution that blocks both edges of the capillary, while its external surface is cleaned with 2-propanol. Then a Karl Suss aligner exposure tool is used to expose two locations of the external capillary surface. For the selection of the exposed regions, two "rings" of 0.5 cm length each one (1 cm distant each other and at 2 cm distance of each one from the capillary edge) are not covered and the other regions of the external capillary surface are covered with a non-transparent tape. Thus, the capillary is exposed for 1 min, then turned 60° around its axis, exposed again for 1 min, turned 60°, and so on until the whole film is irradiated (the capillary is turned 6 times by 60° each time and exposed 1 min for each time, too). Afterwards, the opaque tape is removed and the tube is baked at 60° C. for 5 min into aluminum plate holes of similar size with the capillary. Then a $2.7\times10^{-3}$ N aqueous solution of tetramethyl ammonium hydroxide (TMAH) is introduced in a continuous way into the capillary: 4 times by 2 ml solution each time, twice from each edge and with 5 min total time of the development. The washing of the capillary with deionized water is followed with the same continuous way (4×2 ml for 5 min) and the tube is dried under a nitrogen stream. Then, a 20 mg/L rabbit IgG solution in 0.04 M phosphate buffer, pH 6.5, is introduced into the capillary and incubated for 30 min. The capillary is washed with deionized water as described above (4×2 ml for 5 min) and dried with nitrogen stream. Subsequently the whole capillary is exposed with the previous manner (6×1 min exposure dose with 60° turn of the capillary each time). After that it is baked at 60° C. for 5 min in the aluminum plate with the holes. Next a $2.7\times10^{-3}$ N aqueous TMAH solution is introduced into the capillary as described above (4×2 ml for 5 min), it is washed with deionized water with the same manner and dried under a nitrogen stream. Then a 10 g/L bovine serum albumin in 0.1 M $NaHCO_3$ buffer, pH 8.5, is incubated in the tube for 1 hr; subsequently the capillary is dried with nitrogen. At the end of the lithographic process two distinct "zones" of rabbit IgG (active protein) are formed and the other areas of capillary inert surface are covered with bovine serum albumin (inert protein).

For the visualization of the above "bands" the capillary is filled with a 5 mg/L goat anti-rabbit IgG-fluorescein isothiocyanate conjugate solution in 0.15 M Tris-HCl buffer, pH 8.25, containing 1 g/L bovine serum albumin, 0.5 g/L bovine IgG, 1 M KCl and 0.2 g/L ethylmercury-thiosalicylic acid sodium salt, and incubated for 30 min, at 22° C. Then it is washed (4×1 ml) with a 0.01 M Tris-HCl buffer, pH 8.25 containing 0.05% (v/v) Tween 20 and dried under a nitrogen stream. Afterwards, the capillary is filled with the same washing solution, and the fluorolabeled immunocomplex formed on the internal capillary surface was determined by scanning the capillary perpendicularly with a specific optical set-up constructed in our laboratory. Two distinct signals are obtained indicating two areas with the fluorolabeled immunocomplex formed.

REFERENCES

1. M. M. Thompson et al., "Biosensors and the transduction of molecular recognition", Anal. Chem., 63, 393 A, 1991.
2. E. P. Diamandis, T. K Christopoulos eds, "Immunoassay", San Diego, Academic Press, 1996.
3. J. M. McAlear et al., "Microdevice substrate and method for making micropattern devices", U.S. Pat. No. 4,103, 064, 1978.
4. J. M. McAlear et al., "Microsubstrates and method for making micropattern devices", U.S. Pat. No. 4,103,073, 1978.
5. Y. Hanazato et al., "Glucose sensor based on a field-effect transistor with a photolithographically patterned glucose oxidase membrane", Anal. Chim. Acta, 193, 87-96, 1987.
6. T. Vopel et al., "Amperometric glucose sensor with a photolithographically patterned enzyme membrane", Anal. Chim. Acta, 251, 117-120, 1991.
7. Y. Miyahara et al., Sensors Actuators, 7, 1, 1985.
8. S. Britland et al., "Micropatterned proteins and synthetic peptides on solid supports: a novel application for microelectronics fabrication technology", Biotechnol. Prog., 8, 155-160, 1992.
9. D. Kleinfeld et al., "Controlled outgrowth of dissociated neurons on patterned substrates", J. Neurosci., 4098-4120, 1988.
10. D. W. Conrad et al., "Photoactivatable polymers for producing patterned biomolecular assemblies", U.S. Pat. No. 5,736,257, 1995.
11. D. W. Conrad et al., "Photoactivatable polymers for producing patterned biomolecular assemblies", U.S. Pat. No. 5,847,019, 1998.
12. H. Gao et al., "Immunosensing with photoimmobilized immunoreagents on planar optical wave guides", Biosens. and Bioelectronics, 10, 317, 1995.
13. D. V. Nicolau et al., "Positive and negative tone patterning using conventional Deep-UV/e-beam resists", Langmuir, 15, 3845, 1999.
14. E. D. Fabrizio et al., "Nanometer biodevice fabrication by electron beam lithography", J. Vac. Sci. Technol. B, 15(6) November/December 1997.
15. C. S. Dulsey et al., "Deep UV photochemistry of chemisorbed monolayers: patterned coplanar molecular assembies", Science, 551, April 1991.
16. D. A. Stenger et al., "Coplanar molecular assemblies of amino- and perfluorinated alkylsilanes: characterization and geometric definition of mammalian cell adhesion and growth", J. Am. Chem. Soc., 114, 8435, 1992.
17. S. K. Bhatia et al., "New approach to producing patterned biomolecular assemblies", J. Am. Chem. Soc., 114, 4432, 1992.
18. S. K. Bhatia et al., "Fabrication of surfaces resistant to protein adsorption and application to two-dimensional protein patterning", Anal. Biochemistry, 208, 197, 1993.
19. D. W. Conrad et al., "Photoactivatable o-nitrobenzyl polyethylene glycol-silane for the production of patterned biomolecular arrays", U.S. Pat. No. 5,773,308, 1998.
20. O. Buchardt et al., "Photochemical surface modification of polystyrene in the presence of cerium(IV) ammonium nitrate: improved binding of proteins, amines and mercaptans in the presence of detergent", Biotechnol. Appl. Biochem., 1, 223, 1993.
21. H. I. Elsner et al., "Use of psoralens for covalent immobilization of biomolecules in solid phase assays", Bioconjugate Chem., A, 463, 1994.
22. M. Maeda et al., "Psoralen-containing vinyl monomer for conjugation of double-helical DNA with vinyl polymers", Bioconjugate Chem., 5, 527, 1994.
23. I. Wilner et al., "Photoswitchable biomaterials: en route to optelectronic systems", Acc. Chem. Research, 30(9) 347, 1997.
24. D. J. Pritchard et al., "Simultaneous determination of follicle stimulating hormone and luteinising hormone using a multianalyte immunosensor", Anal. Chim. Acta, 310, 251, 1995.
25. S. P. A. Fodor et al., "Light directed, spatially addressable parallel chemical synthesis", Science, 251, 767, 1991.
26. G. McGall et al., "Light-directed synthesis of high-density oligonucleotide arrays using semiconductor photoreists", Proc. Natl. Acad. Sci. USA, 93, 13555, 1996.
27. P. Morales et al., "New method of deposition of biomolecules for bioelectronic purposes", Appl. Phys. Lett., 64, 1042, 1994.
28. G. V. Shivashankar et al., "Biomolecular recognition using submicron laser lithography", Appl. Phys. Lett., 7, 417, 1998.
29. E. Delamarche et al., "Patterned Delivery of Immunoglobulins to Surfaces Using Microfluidic Networks", Science, 276, 779, 1997.
30. G. MacBeath et al., "Printing proteins as microarrays for high-throughput function determination", Science, 289, 1760, 2000.
31. P. Argitis et al., "Biocompatible lithographic processes and materials for patterning of biomolecules", GR. Patent 1003421, 1999.
32. A. Douvas et al., "Biocompatible photolithographic process for the patterning of biomolecules", Biosens. and Bioelectronics, 2001, in press.

The invention claimed is:

1. A kit of photolithographic processing reagents comprising: (1) photoresist comprising a copolymer synthesized from monomers, wherein at least one of said monomers is 2-hydroxyethyl-methacrylate and wherein at least one of said monomers contains an acid cleavable group and at least one of said monomers contains a hydrophilic group selected from the class of hydroxyls and carboxyls; and (2) dilute aqueous base developer of less than 0.01 N base concentration.

2. Method of photolithographic processing using photoresist comprising a copolymer synthesized from monomers, wherein at least one of said monomers contains an acid cleavable group and at least one of said monomers contains a hydrophilic group selected from the class of hydroxyls and carboxyls, comprising the steps of exposure of selected photoresist areas, dissolution of said photoresist areas and deposition of biomolecules on the substrate, wherein the step of dissolution is accomplished using dilute aqueous base developer that is less than 0.01 N base concentration and wherein exposure of selected photoresist areas and the subsequent dissolution of said photoresist areas follows the deposition of biomolecules on the substrate without deactivating the deposited biomolecules.

3. Method according to claim 2, wherein the exposure of selected photoresist areas and the subsequent dissolution of said photoresist areas is repeated more than once without deactivating the deposited biomolecules.

4. Method of photolithographic processing using photoresist comprising a copolymer synthesized from monomers of 2-hydroxyethyl- methacrylate, isobornyl-methacrylate, t-butylmethacrylate, and acrylic acid, wherein the method comprises the steps of exposure of selected photoresist areas, dissolution of said photoresist areas and deposition of biomolecules on the substrate.

5. Photoresist in contact with a developer wherein said photoresist comprises a copolymer synthesized from monomers, wherein at least one of said monomers is 2-hydroxyethyl-methacrylate and wherein at least one of said monomers contains an acid cleavable group and at least one of said monomers contains a hydrophilic group selected from the class of hydroxyls and carboxyls; and wherein said developer is dilute aqueous base developer of less than 0.01 N base concentration.

6. Method of photolithographic processing comprising the steps of exposure of selected photoresist areas, dissolution of said photoresist areas and deposition of biomolecules on a substrate wherein the step of dissolution is accomplished with the photoresist in contact with a developer, as recited in claim 5.

7. Method of photolithographic processing for micropatterning biomolecules that are proteins or nucleic acid chain parts on a substrate comprising the steps of exposure of selected photoresist areas, dissolution of said photoresist areas and deposition of biomolecules on the substrate wherein the step of dissolution is accomplished with a photoresist in contact with a developer, as recited in claim 5.

8. The photoresist comprising a copolymer synthesized from monomers of 2-hydroxyethyl-methacrylate, isobornyl-methacrylate, t-butylmethacrylate, and acrylic acid wherein the proportion of 2-hydroxyethyl-methacrylate/isobornyl-ethacrylate/t-butylmethacrylate/acrylic acid is 30/40/20/10 by weight.

* * * * *

UNITED STATES PATENT AND TRADEMARK OFFICE

CERTIFICATE OF CORRECTION

PATENT NO. : 7,608,389 B2
APPLICATION NO. : 10/479293
DATED : October 27, 2009
INVENTOR(S) : Panagiotis Argitis et al.

It is certified that error appears in the above-identified patent and that said Letters Patent is hereby corrected as shown below:

Title Page;
On the front page of the patent, item (75) please add the following inventor data: "Antonios Douvas, Institute of Microelectronics, NCSR "Demokritos" Aghia Paraskevi, Athens (GR) GR-15310"

On the front page of the patent, item (75) after inventor Constantinos D. Diakoumakos, please insert the following data: --Institute of Microelectronics, NCSR "Demokritos" Aghia Paraskevi, Athens (GR) GR-15310--

Signed and Sealed this

Thirteenth Day of April, 2010

David J. Kappos
*Director of the United States Patent and Trademark Office*